(12) United States Patent
Keyes et al.

(10) Patent No.: US 9,486,722 B2
(45) Date of Patent: Nov. 8, 2016

(54) SOLID-LIQUID SEPARATION WITH A NO-DRY ROTARY PRESSURE FILTER

(71) Applicant: BP Corporation North America Inc., Naperville, IL (US)

(72) Inventors: Timothy Keyes, Madison, AL (US); Thomas Bartos, Naperville, IL (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 14/585,779

(22) Filed: Dec. 30, 2014

(65) Prior Publication Data

US 2015/0182890 A1 Jul. 2, 2015

Related U.S. Application Data

(60) Provisional application No. 61/922,247, filed on Dec. 31, 2013.

(51) Int. Cl.
| | |
|---|---|
| *C07C 51/42* | (2006.01) |
| *B01D 33/60* | (2006.01) |
| *C07C 51/47* | (2006.01) |
| *B01D 33/073* | (2006.01) |
| *B01D 33/62* | (2006.01) |

(52) U.S. Cl.
CPC ............. *B01D 33/60* (2013.01); *B01D 33/073* (2013.01); *B01D 33/62* (2013.01); *C07C 51/47* (2013.01)

(58) Field of Classification Search
CPC ....... C07C 51/47; C07C 51/43; C07C 63/26; B01D 33/073; B01D 33/60; B01D 33/62
See application file for complete search history.

(56) References Cited

U.S. PATENT DOCUMENTS

| | | | |
|---|---|---|---|
| 2,741,369 A | 5/1953 | Fest | |
| 5,175,355 A | 12/1992 | Streich et al. | |
| 5,200,557 A | 4/1993 | Gee et al. | |
| 5,676,847 A | 10/1997 | Yamamoto et al. | |
| 5,676,849 A * | 10/1997 | Sammons | B01D 17/0202 204/450 |
| 5,756,833 A | 5/1998 | Rosen et al. | |
| 6,137,001 A | 10/2000 | Broeker et al. | |
| 7,807,060 B2 | 10/2010 | Schmid | |
| 7,935,844 B2 | 5/2011 | Bartos | |
| 7,935,845 B2 | 5/2011 | Bartos et al. | |
| 8,173,834 B2 | 5/2012 | Bartos | |
| 9,260,370 B2 | 2/2016 | Bartos | |
| 9,315,441 B2 | 4/2016 | Clark et al. | |
| 2005/0051473 A1 | 3/2005 | Suss et al. | |
| 2008/0161599 A1 * | 7/2008 | Lin | C07C 51/487 562/485 |
| 2015/0166452 A1 | 6/2015 | Bartos et al. | |
| 2015/0183709 A1 | 7/2015 | Bartos | |

FOREIGN PATENT DOCUMENTS

| | | | |
|---|---|---|---|
| JP | 2005263653 | * | 9/2005 |
| WO | WO-2016/014830 | | 1/2016 |
| WO | WO-2016/025399 | | 2/2016 |

OTHER PUBLICATIONS

JP653 translated.*

* cited by examiner

*Primary Examiner* — Yevegeny Valenrod
*Assistant Examiner* — Blaine G Doletski
(74) *Attorney, Agent, or Firm* — Robert N. Carpenter

(57) ABSTRACT

A process for recovering a solid product from a solid/liquid mixture. The process includes filtering a solid/liquid mixture to form a filter cake in a first solid-liquid separation zone. The filter cake comprises the solid product. The first solid-liquid separation zone comprises a rotary pressure filter apparatus configured to apply a pressure differential across at least one filter member, and the filter cake is formed on the filter member. The filter cake is then washed with fluid in the rotary filter apparatus to form a wet filter cake. The wet filter cake is then transferred to a reslurrying zone. The wet filter is mixed with a reslurrying fluid to form a slurry, and the slurry is transferred to a second solid/liquid separation zone, where the solid product is separated from the slurry.

10 Claims, 2 Drawing Sheets

SOLID-LIQUID SEPARATION WITH A NO-DRY ROTARY PRESSURE FILTER

CROSS-REFERENCE TO RELATED APPLICATIONS

This application claims priority, under 35 U.S.C. §119(e), of Provisional Application No. 61/922,247, filed Dec. 31, 2013, incorporated herein by this reference.

TECHNICAL FIELD

The present teachings relate generally to solid-liquid separation processes, and in particular, to a solid-liquid separation process utilizing a rotary pressure filter.

BACKGROUND

Multiple-stage separation techniques may result in higher purities of solid products, but may require substantially more investment in equipment. One method to reduce capital expenditures in a multi-stage separation is through the use of a rotary pressure filter. Rotary pressure filter have been designed to perform more than one of the steps of a multiple-stage separation technique in a single piece of equipment. For example, known rotary pressure filters perform a filtration to form a filter cake, followed by a washing of the filter cake. The washed filter cake is then dried before leaving the rotary pressure filter.

Despite these advancements, there continues to be a need to produce highly effective solid-liquid separations while reducing capital expenditures and variable costs for such processes.

SUMMARY

According to one aspect of the invention, a process for recovering a solid product from a solid/liquid mixture is provided in accordance with the present invention. According to another aspect of the invention, the process includes filtering a solid/liquid mixture to form a filter cake in a first solid-liquid separation zone. The filter cake comprises the solid product. The first solid-liquid separation zone comprises a rotary pressure filter apparatus configured to apply a pressure differential across at least one filter member, and the filter cake is formed on the filter member. The filter cake is then washed with fluid in the rotary filter apparatus to form a wet filter cake. The wet filter cake is transferred to a reslurrying zone and mixed with a reslurrying fluid to form a slurry. The slurry is transferred to a second solid/liquid separation zone where the solid product is separated from the slurry.

Other aspects of the present invention will be apparent in view of the description that follows.

DETAILED DESCRIPTION OF THE PREFERRED EMBODIMENTS

By way of general introduction, the present invention is directed an highly effective multi-stage process for recovering a solid product from a solid/liquid mixture. The process is configured to reduce the capital expenditure for equipment and variable costs when compared with conventional processes.

In some embodiments of the invention, the process comprises filtering a solid/liquid mixture to form a filter cake comprising the solid product on a filter member in a rotary pressure filter apparatus configured to apply a pressure differential across the filter member, the rotary pressure filter apparatus defining a first solid/liquid separation zone; washing the filter cake with a wash fluid in the rotary filter apparatus to form a wet filter cake; transferring the wet filter cake to a reslurrying zone and mixing the wet filter cake with a reslurrying fluid to form a slurry; transferring the slurry to a solid/liquid separation zone and separating the solid product from the slurry. In some embodiments, the wet filter cake is transferred from the rotary pressure filter apparatus to the reslurrying zone without drying. In some embodiments, the rotary pressure filter apparatus is configured to operate without a drying zone.

In some embodiments, the solid product is a pharmaceutical or a food component product. In other embodiments, the solid product is a chemical, or in particular, a petrochemical. In some embodiments, the product is an aromatic hydrocarbon such as paraxylene. In other embodiments, the product is an aromatic carboxylic acid, such as terephthalic acid.

The process may be incorporated into new manufacturing plants, or may be retrofitted into existing manufacturing plants by replacing existing equipment, such as centrifuges, washers, and dryers, with a rotary pressure filter apparatus configured to operate with a filtering zone and a washing zone, but not with a drying zone.

The process in accordance with the present invention eliminates the need to install a centrifuge and incur the associated electricity costs. The process also enables filtering and washing on a single piece of equipment.

Figure 1:
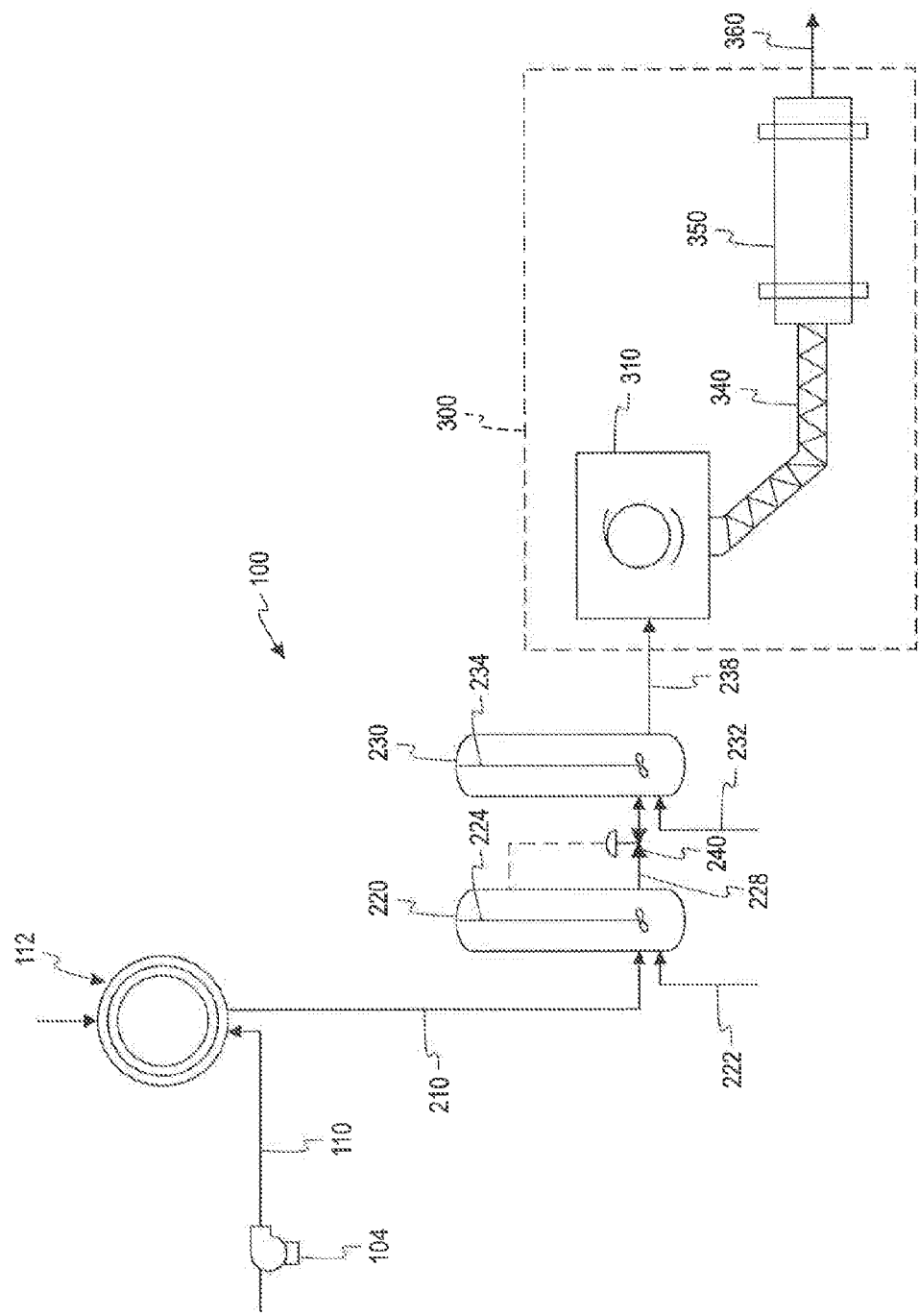
FIG. 1 shows a process flow diagram for a solid-liquid in accordance with one embodiment of the present invention.

Referring now to FIG. 1, a multi-stage process for separating a solid product from a solid-liquid mixture in accordance with one embodiment of the invention is shown generally at 100.

As shown in FIG. 1, a solid-liquid mixture is fed via 110 into a first solid/liquid separation zone comprising a pump 104 and a rotary pressure filter apparatus 112. The solid-liquid mixture in line 110 may comprise effluent from upstream equipment (not shown) that discharges the solid-liquid mixture, for example, from a crystallizer, a reslurrying vessel, a chemical reactor, or a mixer. The solid may be present in any concentration in the solid-liquid mixture. In one embodiment, the solid component comprises 40 to 50 wt % of the solid-liquid mixture.

The rotary pressure filter apparatus 112 operates under a positive pressure to filter and remove the liquid from the solid and collect the solid for further processing. Rotary pressure filter apparatus are generally known in the art and are disclosed, for example, in U.S. Pat. Nos. 2,741,369, 7,807,060 and US Pat. App. 20050051473.

Figure 2:
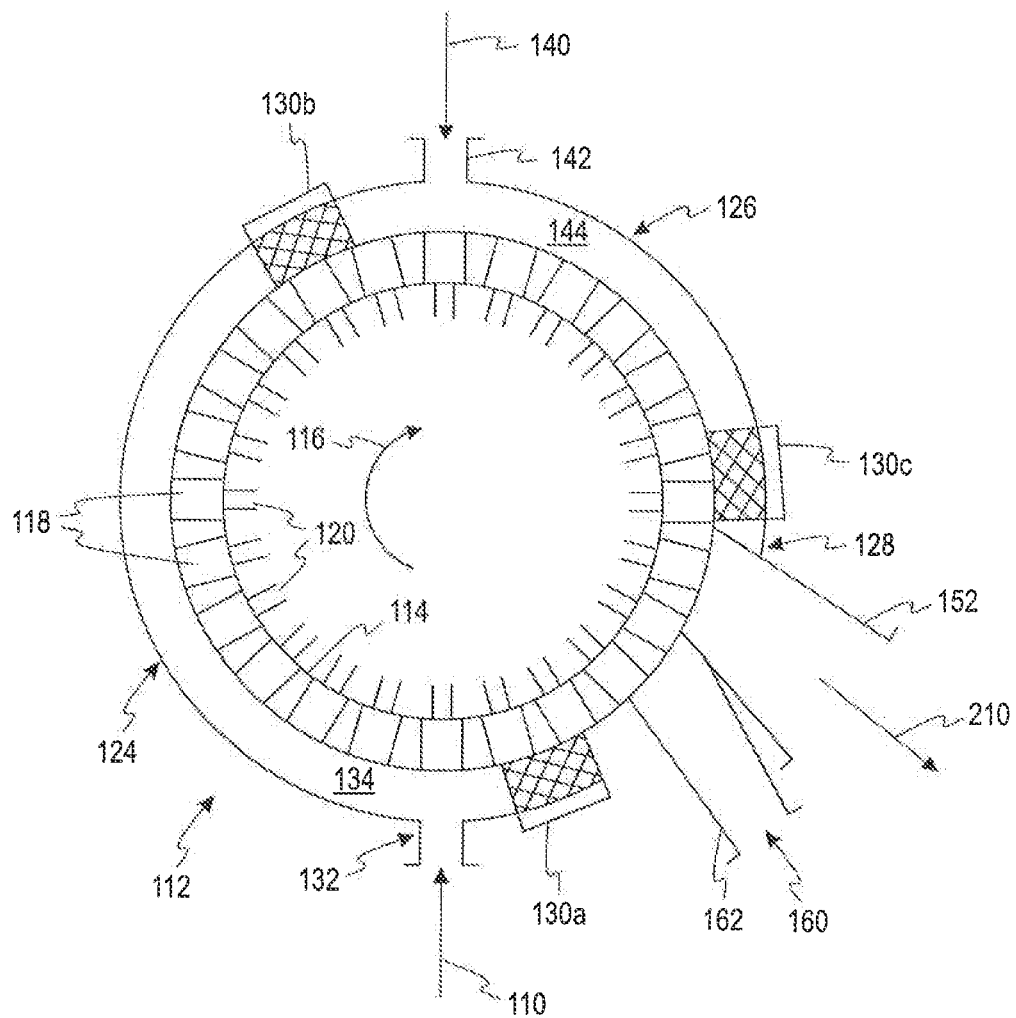
FIG. 2 shows a cross-section of a rotary pressure filter apparatus that is suitable for use in one embodiment of the process according to the present invention.

FIG. 2 illustrates one embodiment of a rotary pressure filter apparatus 112 in accordance with the present invention. As shown in FIG. 2, the rotary pressure filter apparatus 112 comprises a rotating filter drum 114 which rotates as indicated by arrow 116. A plurality of compartments 118 are arranged around the circumference of the filter drum 114 and rotate with the filter drum 114. The compartments 118 each include a filter member (not shown) adjacent the filter drum. In some embodiments the filter member comprises woven fabric. Each compartment 118 also has associated with it a corresponding outlet pipe 120 which also rotates with the filter drum 114 and the compartments 118. The outlet pipes 120 are configured such that filtrate from each compartment 116 passes through its corresponding filter member adjacent the filter drum 114 and into its corresponding outlet pipe.

The rotary pressure filter apparatus 112 also include a number of stationary components. The rotary pressure filter apparatus 112 is divided into a plurality of zones, including a filtering zone generally shown at 124, a wash zone generally shown at 126, a discharge zone generally shown at 128. The filtering zone 124 defines the first stage of a multi-stage process for separating and recovering a solid product from solid-liquid mixtures. Each of the zones are separated from the adjacent zones by sealing members 130a, 130b, and 130c.

The solid-liquid mixture stream enters the filtering zone 124 of the rotary pressure filter apparatus 112 through inlet 132. The inlet 132 is in fluid communication with plenum 134 which distributes the solid-liquid mixture into compartments 118. In some embodiments, the pressure in the filtering zone is maintained at about 3 bar(g) to about 7 bar(g), and in some embodiments, 5 bar(g) to 6 bar(g). As a result of the pressure differential that is maintained between the compartments 118 and the outlet pipes 120 and across the filter member in the compartments, liquid of the solid-liquid mixture is forced through the filter member in the compartments 118 and into outlet pipes 120. The outlet pipes are in fluid communication with filtrate discharge pipes (not shown) for collecting filtrate. The solid components of the solid-liquid mixture remain on the filter member in the form a filter cake.

The compartments 118 now having filter cake continue their rotation into wash zone 126. A wash fluid stream 140 is introduced into the wash zone 126 through inlet 142. In some embodiments, wash fluid in introduced at a rate of about 0.5 kg to about 1.5 kg of wash fluid per 1 kg of filter cake. The inlet 142 is in fluid communication with plenum 144 which distributes the wash fluid into compartments 118. In some embodiments, the pressure in the wash zone is maintained at about 3 bar(g) to about 7 bar(g), in some embodiments, 5 bar(g) to 6 bar(g). As a result of the pressure differential that is maintained between the compartments 118 and the outlet pipes 120 and across the filter member in the compartments, the wash fluid is forced into the filter cake that resides on the filter member in the compartments 118 to form a wet filter cake. A portion of the wash fluid is removed through the filter member and into the outlet 120, taking with it impurities and residual liquids from the solid-liquid mixture that may have adhered to the filter cake or residing in voids of the filter cake. Another portion of the wash fluid remains with the now wet filter cake. In some embodiments, the wet filter cake comprises about 25 wt % to about 50 wt % residual wash fluid. The wash fluid is selected to remove impurities from the filter cake while not interfering with further processing of the filter cake to recover the final solid product. In one embodiment, the wash fluid comprises water. In another embodiment, the wash fluid comprises condensate from another portion of an integrated process.

The compartments 118 now having wet filter cake continue their rotation into discharge zone 128. The wet filter cake may be discharged by gravity. In some embodiments, the discharge zone 128 includes a filter cake disengaging device (not shown), such as a blower or scraper to assist with the discharge of the wet filter cake. After wet filter cake is removed from the discharge outlet 152, a rinse solution may be injected into inlet 162 in order to clean the filter members of the compartments 118 before they continue into the next cycle through the rotary pressure filter apparatus 112.

Those skilled in the art will appreciate that other configurations of the rotary pressure filter apparatus 112 may be used in accordance with the present invention. For example, the rotary pressure filter apparatus may include multiple filtering zones and multiple wash zones. However, in contrast to a conventional processes, the rotary pressure filter apparatus does not include a drying zone. As a result, the wet filter cake discharged in the discharge zone 126 comprises at least a portion of the wash fluid 140 that is introduced into the washing zone 124.

Referring again to FIG. 1, the wet filter cake exiting the rotary pressure filter apparatus 112 is transferred via line 210 to a reslurrying zone comprising one or more reslurrying vessels 220, 230. In the embodiment shown in FIG. 1, the wet filter cake is transferred to the reslurrying zone without drying the wet filter cake.

Reslurrying fluid is introduced via line 222 into reslurrying vessel 220. The reslurrying vessel 220 is equipped with an agitator 224, and the wet filter cake and the reslurrying fluid is made into a slurry. In the embodiment shown in FIG. 1, the reslurrying zone includes a second reslurrying vessel 230, also equipped with an agitator 234, which receives effluent from the first reslurrying vessel 220 via line 228. The second reslurrying vessel 230 optionally also has an inlet 232 for additional reslurrying fluid. A level-detecting control valve 240 allows passage of slurry between the vessels when the slurry reaches a predetermined level in the first reslurrying vessel. The control valve 240 allows each of the reslurrying vessels to operate at a pressure independent of the other. In this manner, the first reslurry vessel 220 may operate at an elevated pressure equal to the pressure in the rotary pressure filter apparatus 112 as well as equipment upstream of the rotary pressure filter apparatus 112, and the second reslurrying vessel 230 may operate at pressure equal to downstream equipment. In some embodiments, the first reslurry vessel 220 operates at a pressure of about 3 bar(g) to about 7 bar(g), and in some embodiments, about 5 bar(g) to about 6 bar(g).

The reslurrying fluid is selected to remove impurities from the filter cake while not interfering with further processing of the filter cake to recover the final solid product, and to not interact detrimentally with the wash fluid still remaining in the wet filter cake. The reslurrying fluid may be the same or different that the wash fluid. In one embodiment, the reslurrying fluid comprises water. In another embodiment, the reslurrying fluid comprises steam condensate from another part of an integrated process.

The second reslurrying vessel 230 discharges slurry into an outlet line 238. The line 238 transfers the slurry to a second, final solid-liquids separation zone 300. In the embodiment shown in FIG. 1, the solid-liquid separation zone 300 comprises a rotary vacuum filter 310, which receives the slurry and removes a majority of the liquid in the slurry through vacuum filtration. The resulting filter cake exits the rotary vacuum filter and is fed to a screw conveyor 340, which in turn transfers the filter cake to a gas fired rotary dryer 350. Final solid product is removed from the dryer via line 360. Those skilled in the art will appreciate that other equipment may be used in the second solid-liquid separation zone 300, for example, other filtering devices, centrifuges, and dryers may be used.

In some embodiments, the final solid product comprises a substantially pure product with little or no impurities remaining. For example, in some embodiments, the solid product is at least 99% pure on a weight basis. In another embodiment, the solid product is at least 99.7% pure on a weight basis. In another embodiment, the solid product is at least 99.9% pure on a weight basis.

EXAMPLE

In one embodiment of the invention, the solid-liquid mixtures in line 110 is effluent from a crystallizer as part of an integrated process for manufacturing purified terephthalic acid from paraxylene. In this embodiment, the solid-liquid mixture comprises about 40 wt % of solid terephthalic acid, water, and about 1000 ppm impurities such as paratoluic acid, hydroxymethylbenzoic acid, and 4-carboxybenzaldehyde. The solid-liquid mixture is fed to rotary pressure filter apparatus 112 which operates in the filtering zone at about 6 bar(g). After filtration, water is added as a wash fluid and the resulting stream including the wet filter cake exiting the rotary pressure filter apparatus comprises about 30 wt % water. The wet filter cake stream enters the reslurrying vessel 220, which operates at 4 bar(g), and water is introduced as a reslurrying fluid. The resulting slurry is transferred through control valve 240 into a reslurrying vessel 230 operated at ambient pressure, where additional water is introduced as a reslurrying liquid. The slurry exiting the second reslurrying vessel 230 comprises about 50 wt % solid terephthalic acid, about 200 ppm paratoluic acid, about 5 pppm 4-carboxybenzaldehyde, and the remainder water. After removing the filtrate in the rotary vacuum filter 310 and drying the filter cake in dryer 350, the final terephthalic acid product contains less than 150 ppm paratoluic acid, and less than 5 ppm 4-carboxybenzaldehyde.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A process for recovering a solid product from a solid/liquid mixture, comprising:
   filtering a solid/liquid mixture in a first solid/liquid separation zone to form a filter cake, the filter cake comprising a solid product, the first solid-liquid separation zone comprising a rotary pressure filter apparatus configured to operate at a positive pressure and to apply a pressure differential across at least one filter member, the filter cake forming on said at least one filter member; the rotary pressure filter apparatus further being configured to operate without a drying zone;
   washing the filter cake with a wash fluid in the rotary filter apparatus to form a wet filter cake;
   transferring the wet filter cake to a reslurrying zone and mixing the wet filter cake with a reslurrying fluid to form a slurry;
   transferring the slurry to a second solid/liquid separation zone and separating the solid product from the slurry.

2. The process of claim 1, wherein the wet filter cake is transferred from the rotary pressure filter apparatus to the reslurrying zone without drying.

3. The process of claim 1, wherein the second solid/liquid separation zone comprises a rotary vacuum filter.

4. The process of claim 1, wherein the second solid/liquid separation zone further comprises a dryer.

5. The process of claim 1, wherein the wash fluid comprises water.

6. The process of claim 1, wherein the reslurry fluid comprises water.

7. The process of claim 1, wherein solid product comprises an aromatic compound.

8. The process of claim 1, wherein the solid product comprises an aromatic carboxylic acid.

9. The process of claim 1, wherein the solid product comprises terephthalic acid.

10. The process of claim 1, wherein the solid/liquid mixture is transferred to the first solid/liquid separation zone from a crystallization zone where the solid is crystallized.

\* \* \* \* \*